United States Patent [19]

McClain

[11] Patent Number: 5,362,652

[45] Date of Patent: Nov. 8, 1994

[54] SPECTROPHOTOMETRIC DETECTION OF HYDROPEROXIDES IN HYDROCARBONS

[75] Inventor: Robert D. McClain, Sugar Land, Tex.

[73] Assignee: Nalco Chemical Company, Naperville, Ill.

[21] Appl. No.: 156,374

[22] Filed: Nov. 22, 1993

[51] Int. Cl.$^5$ .................... G01N 21/00; G01N 33/00
[52] U.S. Cl. .................... 436/135; 436/60; 436/164; 208/47
[58] Field of Search .................... 208/47; 436/60, 135, 436/164

[56] References Cited

PUBLICATIONS

Banerjee et al., *Analytical Chemistry*, vol. 36, No. 4, Apr. 1964, pp. 792–796.
Baga et al., *Analytica Chimica Acta*, vol. 204, 1988, pp. 349–353.
Davies et al., *Inorganic Chemistry*, vol. 15, No. 3, 1976, pp. 700–703.
Pobiner, *Analytical Chemistry*, vol. 33, No. 10, Sep. 1961, pp. 1423–1426.
Banerjee et al., *Analytical Chemistry*, vol. 36, No. 12, Nov. 1964, pp. 2367–2368.
Reddy et al., *Analytical Chemistry*, vol. 64, No. 19, Oct. 1992, pp. 2273–2276.
Smith et al., *Analytical Chemistry*, vol. 24, No. 2, Feb. 1952, pp. 371–373.
Cornish et al., *Journal of Chromatographic Science*, vol. 19, Feb. 1981, pp. 85–87.
Johnson et al., *Journal of the American Chemical Society*, vol. 109, No. 7, 1987, pp. 1990–1994.
Kminkova et al., *Chemistry and Industry*, vol. 19, Apr. 1969, pp. 519–520.
Fleming et al., *Analytical Chemistry*, vol. 55, 1983, pp. 1625–1626.

*Primary Examiner*—Asok Pal
*Assistant Examiner*—Bekir L. Yildirim
*Attorney, Agent, or Firm*—Robert A. Miller; Joseph B. Barrett; Daniel N. Lundeen

[57] ABSTRACT

A method for the determination of organic hydroperoxides in a hydrocarbon which has been subjected to oxidative polymerization conditions is disclosed. The steps employed in the invention include mixing an organic cupric salt such as cupric acetate and a phenanthroline such as 2,9-dimethyl-1,10-phenanthroline with a sample of the hydrocarbon in an organic solvent such as acetonitrile, measuring the color change after a fixed period of time for cuprous complex formation, and comparing the measurement to the color change of a standard reference to determine the relative quantity of organic hydroperoxide in the sample.

11 Claims, No Drawings

SPECTROPHOTOMETRIC DETECTION OF HYDROPEROXIDES IN HYDROCARBONS

SUMMARY OF THE INVENTION

The present invention is directed to a method for the determination of organic hydroperoxides in a hydrocarbon which contains olefins and has been subjected to oxidative polymerization conditions, and more particularly to a method wherein a sample of the hydrocarbon is subjected to an organic copper salt and a copper complexing compound which forms a colored copper complex and the amount of hydroperoxides is detected by spectrophotometric means.

BACKGROUND OF THE INVENTION

In the petroleum refining and chemical process industries, the oxidative polymerization of olefinic hydrocarbons during processing is a constant problem that leads to the fouling of process equipment which in turn leads to heat transfer loss, increased fuel and power losses, increased downtime for maintenance, and reduced product yield or purity. The oxidative polymerization of olefinic hydrocarbons thus results in the overall effect of reduced profits and increased safety risks.

Oxidative polymerization is a well known free radical process in which hydrocarbon hydroperoxides and hydrocarbon radicals are formed and the hydrocarbon radicals polymerize into gums or cross-linked polymers.

The present invention is a method by which the hydroperoxide content of a hydrocarbon stream can be determined to investigate or evaluate the fouling potential of a stream subjected to conditions that are conducive to fouling. This is important since the type and amount of antifoulant additive to be added to the process stream can be estimated based on its fouling potential. In addition, this method can be used in the laboratory or in the field to monitor process streams on a suitable periodic basis such as once a week to detect possible adverse changes in the process streams before they become a serious and expensive problem.

It is known from Banerjee et al., *Analytical Chemistry* (volume 36, no. 4, April 1964, pp. 792–796), that it is possible to make spectrophotometric determinations of peroxides in organic solvents by using acetic acid, chloroform and potassium iodide with the liberation of iodine. However, this method is rather complex and requires the use of a nitrogen purge as well as more toxic reagents.

It is also known from Baga et al., *Analytica Chimica Acta* (volume 204, 1988, pp. 349–353), that hydrogen peroxide can be spectrophotometrically determined in aqueous solutions using the color change of a copper/2,9-dimethyl-1,10-phenanthroline complex. This method is not applicable to the determination of organic peroxides since they are insoluble in the aqueous media.

SUMMARY OF THE INVENTION

The invention comprises a method for the determination of organic hydroperoxides in a hydrocarbon which contains olefins and has been subjected to oxidative polymerization conditions, wherein the steps comprise adding a mixture of an organic cupric salt and a copper complexing agent, preferably a phenanthroline, to a sample of the hydrocarbon in an organic solvent, measuring the amount of color change after a fixed period of time for cuprous complex formation in the mixture, and comparing the color change to a measurement of the color change of a standard reference to determine the relative quantity of hydroperoxide in the sample. The invention is particularly useful for the determination of up to 1500 parts per billion of organic hydroperoxides in petroleum distillates such as pyrolysis gasoline, stripper bottoms and the like.

The invention also provides an improvement in a method of inhibiting fouling in hydrocarbon processing operations. The method comprises adding a fouling inhibitor to a hydrocarbon that contains olefins, and subjecting the hydrocarbon to oxidative polymerization. The improvement comprises using the above-described method to periodically determine the relative quantity of hydroperoxides in a sample of the hydrocarbon, preferably a sample free of the fouling inhibitor. Then, the rate of addition of the fouling inhibitor to the hydrocarbon is increased or decreased relative to any change in the hydroperoxide content from previous determinations thereof.

DESCRIPTION OF THE INVENTION

The method of this invention is applicable to any hydrocarbon fluid that is known to have or is suspected to have, organic hydroperoxides contained therein. It is especially useful with petroleum residues such as the residues of reformers, hydrocrackers, depropanizers, debutanizers and the like. In particular, the hydroperoxide and fouling tendencies can be determined in debutanizer bottoms, pyrolysis gasoline distillation units, FCC light gasoline distillation units, and stripper bottoms (primarily comprising acetonitrile) in a butadiene plant.

Organic solvents useful in this invention are those in which the hydrocarbons and the organic copper compounds are mutually soluble. Examples of these solvents are dimethylformamide, acetonitrile, dimethylsulfoxide, isopropanol, and the like.

Useful copper complexing agents can include any soluble organic compound which complexes with copper to form a colored complex which can be observed spectrophotometrically, such as, for example, bipyridines, phenanthrolines and the like. Useful phenanthroline compounds for this process are phenanthroline itself and 2,9-dimethyl-1,10-phenanthroline (DMP).

The useful organic copper compounds that can be used are cupric acetate monohydrate, cupric bromide, cupric stearate, cupric naphthenate, and similar compounds soluble in organic media.

The hydrocarbon fluid is sampled for spectrophotometric analysis using conventional sampling techniques well known in the art, such as, for example, filling a jar, bottle or other suitable container with a representative specimen, introducing a specimen into the inlet or mixing port of an on-line spectrophotometer, or the like. If necessary, the specimen can be pre-treated by, for example, caustic washing or silica absorption, to remove inhibitors or other additives which may be present in the specimen. Some inhibitors and other additives can affect the test results. Relative test results in the presence of such inhibitors can sometimes be useful, but running the test with and without the inhibitor present can indicate the influence of the inhibitor. In any case, the specimen of hydrocarbon fluid is mixed with the copper compound and the copper complexing agent, and diluted in an organic solvent as previously mentioned, preferably with sufficient dilution so that the hydroperoxide content of the specimen-solvent mixture is in the range up to about 1500 parts per billion by weight. The diluted specimen can contain more than this preferred level of hydroperoxide, but higher levels are less preferred since the proportionality of absorbance to hydroperoxide content is less linear.

The amount of copper compound and copper complexing agent used should be a suitable stoichiometric excess to react with all of the organic hydroperoxide present in the hydrocarbon fluid specimen. Thus, the amount of copper and copper complexing agent will depend on the amount of specimen mixed therewith, as well as the dilution with the solvent. Generally, the initial concentration of copper (II) and DMP in the diluted mixture ranges from about 0.05 millimolar to about 50 millimolar. The specimen is generally diluted in the mixture at a volume ratio of specimen:mixture from about 1:10,000 to about 1:10, preferably from about 1:500 to about 1:50.

The amount of hydroperoxide in the mixture is determined using spectrophotometric analysis techniques well known in the art, following a predetermined period of time after preparation of the mixture. In contrast to most aqueous systems, the formation of the spectrophotometrically active copper complex in the organic hydroperoxide mixtures of the present invention is a generally kinetic phenomenon and continues to change with time. In general, a sufficient time must be allowed for formation of enough copper complex for spectrophotometric measurement, but if too much time elapses, the spectrophotometric measurement may not be linearly proportional to the amount of organic hydroperoxide in the specimen. The period of time which elapses after mixture of the copper, complexing agent and organic hydroperoxide specimen is preferably from about 5 minutes to about 240 minutes, more preferably from 15 minutes to 90 minutes.

Measurement of color change, or absorbance of the mixture is done generally at the peak absorbance wavelength. For copper-DMP complex, an absorbance wavelength at 454 nm is suitable. The wavelength for spectrophotometric measurements can be selected, not necessarily to give the maximum absorbance, but also for obtaining linear proportionality.

In general, a solution of the copper compound, copper complexing agent and solvent is used as a blank reference to zero a conventional spectrophotometer (0% organic hydroperoxide, 0% relative absorbance), and a standard reference is used to set the absorbance to a preset reading, e.g. 100% or 50% relative absorbance, or a range of standard references can be used to obtain a calibration curve. However, if the absorbance and background settings of the spectrophotometer are kept the same, the amount of, hydroperoxide can be determined based on the known absorbance of copper complexing agent-specimen mixtures relative to the absorbance of the standard reference.

The invention is further illustrated by the following examples.

EXAMPLE 1

A solution of 2.64 wt % copper(II) acetate monohydrate was prepared in acetonitrile. A similar 1.0 wt % solution of 2,9-dimethyl-1,10-phenanthroline (DMP) was prepared. It is to be noted that DMP also has the trivial name neocuproine.

One ml of each of these solutions was added to seven 10 ml flasks. At five minute intervals, 0, 20, 40, 60, 80 and 100 μL of a 100 ppm t-butylhydroperoxide solution were added to six of the seven flasks, respectively. The samples were diluted to 10 ml with acetonitrile immediately after the peroxide addition to form reference standards. Absorbance at 454 nm was recorded exactly one hour after the preparation of the samples.

Five minutes after the last standard was prepared, an aliquot of the bottoms from a debutanizer column was added to the seventh flask and diluted to 10 ml with acetonitrile. The hydroperoxide in the debutanizer bottoms reduced the $Cu^{+2}$ ions to $Cu^{+1}$ ions which formed the visible Cu(DMP) complex.

A standard reference plot of t-butylhydroperoxide concentration versus absorbance was calculated by the method of least squares. The hydroperoxide number (parts per billion of hydroperoxide, assuming the hydroperoxides in the sample have the same molecular weight as t-butylhydroperoxide) of the debutanizer bottoms sample was calculated from this plot and found to be 7735.

The oxidative fouling potential of the debutanizer bottoms specimen was determined by heating 25 ml of a sample of the stream for 2 hours at a temperature of 100° C. in an oxygen atmosphere at 0.69 MPa (gauge) (100 psig) and the amount of gum was determined. Another sample was heated for 2 hours at a temperature of 150° C. under 0.69 MPa (gauge) (100 psig) nitrogen gas and the amount of gum was determined.

When the weight of the oxygen gum was divided by the weight of the nitrogen gum, the ratio was 3.05 and this is taken as the oxidative fouling potential which correlates very well with the high amount of hydroperoxide found in the sample and thus shows the validity and usefulness of the present invention.

EXAMPLE 2

The procedures of Example 1 were repeated with the bottoms from a similar but different debutanizer column. The hydroperoxide number was found to be 3221, and the oxidative fouling potential was 1.64.

EXAMPLE 3

The procedures of Example 1 were repeated with a pyrolysis gas stream. The hydroperoxide number was found to be 2035, and the oxidative fouling potential was 1.36.

EXAMPLE 4

The procedures of Example 1 were repeated with another pyrolysis gas stream. The hydroperoxide number was found to be 737, and the oxidative fouling potential was 0.95.

EXAMPLE 5

The procedures of Example 1 were repeated with a light gasoline fraction from a fluid catalytic cracker (FCC) unit. The hydroperoxide number was found to be 189, and the oxidative fouling potential was 0.

EXAMPLE 6

The procedures of Example 1 were repeated with another light gasoline fraction from a different FCC unit. The hydroperoxide number was found to be 128, and the oxidative fouling potential was 0.

EXAMPLE 7

The procedure of Example 1 was repeated with a commercial acetonitrile stream. The hydroperoxide number was found to be 64, and the oxidative fouling potential was 0.

EXAMPLE 8

The feed to the debutanizer column of Example 1 is continuously treated by addition of 10–500 ppm BHT. A week later, continuing with the same treatment, the hydroperoxide content is determined to be higher, and the antifoulant addition rate is increased to effectively control the increased fouling tendency of the stream.

The foregoing description of the invention is illustrative and explanatory thereof. Various changes in the materials, apparatus, and particular parts employed will occur to those skilled in the art. It is intended that all such variations within the scope and spirit of the appended claims be embraced thereby.

I claim:

1. A method for the determination of organic hydroperoxides in a hydrocarbon which contains olefins and the hydrocarbon has been subjected to oxidative polymerization conditions, comprising the steps of:
   (A) mixing an organic cupric salt and a copper complexing agent with a sample of a hydrocarbon in an organic solvent selected from the group consisting of dimethylformamide, acetonitrile, dimethylsulfoxide and isopropanol;
   (B) measuring the color change after a fixed period of time for cuprous complex formation in the mixture; and
   (C) comparing the measurement of step (B) to a measurement of the color change of a standard reference after said fixed period of time to determine the quantity of hydroperoxide in the sample relative to said standard reference.

2. The method of claim 1, wherein the copper complexing agent is phenanthroline.

3. The method of claim 1, wherein the copper complexing agent is 2,9-dimethyl-1,10-phenanthroline.

4. The method of claim 1, wherein the hydrocarbon is a petroleum distillate containing olefins.

5. The method of claim 1, wherein the organic cupric salt is cupric acetate.

6. The method of claim 1, wherein the organic solvent is acetonitrile.

7. The method of claim 1, wherein the mixture from step (A) has a hydroperoxide number up to about 1500.

8. The method of claim 1, wherein the period of time is fixed at from about 5 minutes to about 240 minutes.

9. The method of claim 1, comprising pretreating the hydrocarbon sample to remove any inhibitors prior to said mixing step (A).

10. A method for the determination of organic hydroperoxides in a petroleum distillate which comprises:
    (A) mixing cupric acetate and 2,9-dimethyl-1,10-phenanthroline with a sample of the distillate in an organic solvent selected from the group consisting of dimethylformamide, acetonitrile, dimethylsulfoxide and isopropanol;
    (B) measuring the color change after a fixed period of time ranging from 5 to 240 minutes for cuprous complex formation with the phenanthroline in the mixture; and
    (C) comparing the color change of the mixture of step (B) to a measurement of the color change of a standard reference after the same period of time to determine the relative quantity of hydroperoxide in the sample.

11. The method of claim 10, wherein the organic solvent is acetonitrile.

* * * * *